United States Patent [19]

Pfluger et al.

[11] Patent Number: 4,958,030
[45] Date of Patent: Sep. 18, 1990

[54] PROCESS FOR THE PREPARATION OF 3-PHENYLPYRROLE DERIVATIVES

[75] Inventors: Rudolf W. Pfluger, Zeiningen; Jean Indermühle, Basel; Franz Felix, Münchenstein, all of Switzerland

[73] Assignee: Ciba-Geigy Corporation, Ardsley, N.Y.

[21] Appl. No.: 419,793

[22] Filed: Oct. 11, 1989

Related U.S. Application Data

[63] Continuation-in-part of Ser. No. 283,341, Dec. 12, 1988, abandoned.

[51] Int. Cl.$^5$ ............................................. C07D 207/02
[52] U.S. Cl. .................................... 548/526; 548/531; 548/537; 548/539; 548/540; 548/561
[58] Field of Search ............... 548/526, 531, 537, 539, 548/540, 561

[56] References Cited

U.S. PATENT DOCUMENTS

| | | | |
|---|---|---|---|
| 4,680,413 | 7/1987 | Genda et al. | 548/561 |
| 4,705,801 | 11/1987 | Martin et al. | 548/561 X |
| 4,778,901 | 10/1988 | Martin | 548/561 |

FOREIGN PATENT DOCUMENTS

| | | | |
|---|---|---|---|
| 0324336 | 7/1989 | European Pat. Off. | |
| 1030571 | 2/1986 | Japan | 548/561 |

Primary Examiner—Joseph Paul Brust
Attorney, Agent, or Firm—Kevin T. Mansfield

[57] ABSTRACT

3-Phenylpyrrole derivatives of formula I

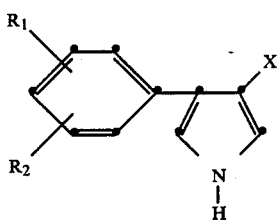

wherein
X is cyano, —CO—R$_3$, —CO—OR$_3$ or $$-\overset{\overset{\displaystyle O}{\|}}{C}-NH-R_4,$$

R$_1$ and R$_2$ are each independently of the other hydrogen, C$_1$-C$_6$alkyl, C$_1$-C$_6$alkoxy, C$_1$-C$_6$alkylthio, nitro, cyano, halogen or C$_1$-C$_6$haloalkyl, or R$_1$ and R$_2$, when taken together, are methylenedioxy or difluoromethylenedioxy, R$_3$ is C$_1$-C$_6$alkyl, C$_1$-C$_6$haloalkyl, phenyl or benzyl, or phenyl or benzyl which are each substituted by halogen, methyl, methoxy or methylthio, and R$_4$ is hydrogen, C$_1$-C$_6$alkyl, C$_1$-C$_6$haloalkyl, phenyl or benzyl, or phenyl or benzyl which are each substituted by halogen, methyl, methoxy or methylthio, are prepared by (a) reacting N-(p-tolylsulfonyl)methyl formamide, in an inert solvent and in the presence of an organic base, with phosphoroxy chloride, mixing the reaction solution with water, separating the aqueous phase of the resultant two-phase mixture, and (b) reacting the organic phase containing (p-tolylsulfonyl)methyl isocyanide direct with a compound of formula II

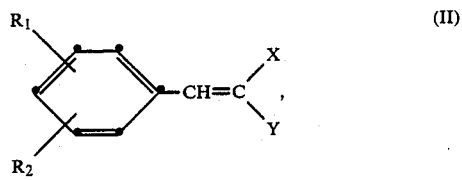

wherein X, R$_1$ and R$_2$ are as defined for formula I, Y is —CO—NHR$_4$, —CO—R$_5$ or —S—R$_5$, R$_5$ is C$_1$-C$_6$alkyl, C$_1$-C$_6$haloalkyl, phenyl or benzyl, or phenyl or benzyl which are each substituted by halogen, methyl, methoxy or methylthio, and R$_4$ is as defined for formula I, in the presence of a base.

26 Claims, No Drawings

PROCESS FOR THE PREPARATION OF 3-PHENYLPYRROLE DERIVATIVES

This is a continuation-in-part of my application, Ser. No. 283,341, filed Dec. 12, 1988, now abandoned.

The present invention relates to a novel process for the preparation of 3-phenylpyrrole derivatives of formula I

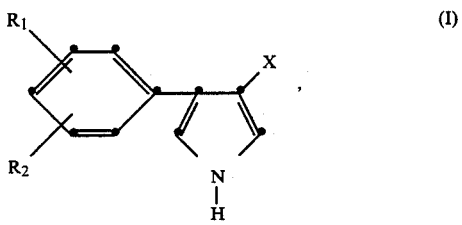

wherein
X is cyano, —CO—$R_3$, —CO—O$R_3$ or

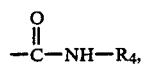

$R_1$ and $R_2$ are each independently of the other hydrogen, $C_1$–$C_6$alkyl, $C_1$–$C_6$alkoxy, $C_1$–$C_6$alkylthio, nitro, cyano, halogen or $C_1$–$C_6$haloalkyl, or $R_1$ and $R_2$, when taken together, are methylenedioxy or difluoromethylenedioxy,
$R_3$ is $C_1$–$C_6$alkyl, $C_1$–$C_6$haloalkyl, phenyl or benzyl, or phenyl or benzyl which are each substituted by halogen, methyl, methoxy or methylthio,
$R_4$ is hydrogen, $C_1$–$C_6$alkyl, $C_1$–$C_6$haloalkyl, phenyl or benzyl, or phenyl or benzyl which are each substituted by halogen, methyl, methoxy or methylthio.

Alkyl will be understood as meaning straight chain or branched alkyl. Examples of suitable $C_1$–$C_6$alkyl radicals are: methyl, ethyl, n-propyl, isopropyl, n-butyl, isobutyl, sec-butyl, tert-butyl, n-pentyl or the pentyl isomers, hexyl or the hexyl isomers. Preferred alkyl radicals are those containing not more than 4 carbon atoms.

Halogen by itself or as moiety of a substituent, as in halobenzyl, halophenyl or haloalkyl, will be understood as meaning fluoro, chloro or bromo, preferably fluoro or chloro. Haloalkyl is typically chloromethyl, fluoromethyl, difluoromethyl, trifluoromethyl, 2-chloroethyl, 2,2,2-trifluoroethyl, 1,1,2,2-tetrafluoroethyl, pentafluoroethyl, 1,1,2-trifluoro-2-chloroethyl, 2,2,2-trifluoro-1,1-dichloroethyl, pentachloroethyl, 3,3,3-trifluoropropyl, 2,3-dichloropropyl, 1,1,2,3,3,3-hexafluoropropyl, 1-chloropentyl, 1-chlorohexyl, and is especially fluoromethyl, chloromethyl, difluoromethyl or trifluoromethyl.

Examples of substituted benzyl and phenyl groups are: 2-chlorophenyl, 3-chlorophenyl, 4-chlorophenyl, 2,4-dichlorophenyl, 3,4-dichlorophenyl, 2,3-dichlorophenyl, 2,4,6-trichlorophenyl, 2,5-dichlorobenzyl, 4-fluorophenyl, 2-fluorobenzyl, 4-methylphenyl, 2,4-dimethylphenyl, 4-trifluoromethylphenyl, 4-bromobenzyl, 4-methoxyphenyl, 2,4-dimethoxyphenyl and 4-methylthiophenyl.

Alkoxy is typically methoxy, ethoxy, n-propoxy, isopropoxy or the four butoxy isomers, n-pentyloxy or the pentyloxy isomers, n-hexyloxy or the hexyloxy isomers, and is preferably methoxy, ethoxy or isopropoxy.

Alkylthio is, for example, methylthio, ethylthio, n-propylthio, isopropylthio or the four butylthio isomers, n-pentylthio or the pentylthio isomers, n-hexylthio or the hexylthio isomers, and is preferably methylthio.

A 3-phenylpyrrole derivative of formula I, wherein $R_1$ and $R_2$, when taken together, are difluoromethylenedioxy and X is cyano, is disclosed as microbicide in European patent application A-No. 206 999.

3-Phenylpyrrole derivatives of formula I, wherein $R_1$ and $R_2$, are each independently of the other hydrogen, halogen, methoxy or methylthio, and X is cyano, are disclosed in European patent application A No. -133 247 as intermediates for the synthesis of microbicides.

In European patent application A- No. 236 272 it is disclosed that the compound of formula I, wherein $R_1$ is 2-chloro, $R_2$ is 3-chloro and X is cyano, has a pronounced fungicidal activity.

According to a process described in Tetrahedron Letters (1972) 52, 5337-5340, cinnamonitrile (formula III)

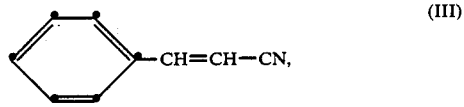

is cyclised with (p-tolylsulfonyl)methyl isocyanide (TOSMIC, formula IV)

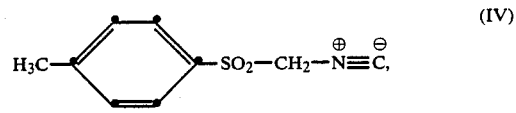

in the presence of a strong base such as sodium hydride, to a 4-cyano-3-phenylpyrrole of formula (V)

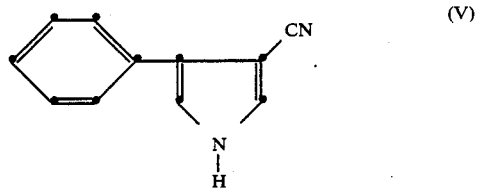

Aside from the yield of only 35%, which is very low for syntheses on an industrial scale, an essential shortcoming of this process is that it can only be carried out with isolated, recrystallised (p-tolylsulfonyl)methyl isocyanide. The handling of isolated, recrystallised (p-tolylsulfonyl)methyl isocyanide is, however, associated with a very high safety risk, for the compound is liable to undergo explosive decomposition at elevated temperature.

Further, the necessary completely anhydrous conditions under which the reaction is carried out make the described process expensive and complicated. On account of these shortcomings, this process is not suitable for the industrial production of 3-phenylpyrrole derivatives of formula I.

Japanese Patent Kokai Sho No. 61-30571 discloses a process for the preparation of 4-cyano-3-phenylpyrroles of formula VI

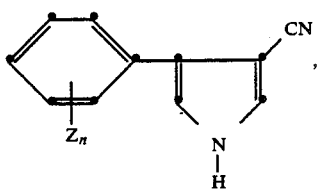

(VI)

wherein Z is halogen, alkyl, haloalkyl, alkylamino, alkoxy, nitro, cyano or methylenedioxy, and n is 0, 1 or 2, by reacting a cyanocinnamate of formula VII

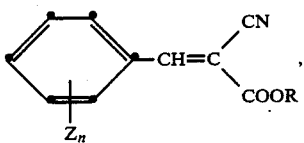

(VII)

wherein Z and n are as defined above and R is hydrogen or alkyl, with (p-tolylsulfonyl)methyl isocyanide in the presence of a base.

Like the process previously described, this process has the serious disadvantage that only isolated, purified, recrystallised (p-tolylsulfonyl)methyl isocyanide can be used for synthesizing the compound of formula VI in satisfactory yield. As already mentioned, crystalline (p-tolylsulfonyl)methyl isocyanide is thermolabile and liable to deflagration and, on account of the acute danger of explosion, is a considerable source of hazard in syntheses carried out on an industrial scale.

There has now been found a novel process which makes it possible to prepare compounds of formula I on an industrial scale, in good yield, in a non-hazardous and economically advantageous manner.

The novel process of this invention for the preparation of 3-phenylpyrrole derivatives of formula I comprises (a) reacting N-(p-tolylsulfonyl)methyl formamide, in an inert solvent and in the presence of an organic base, with phosphoroxy chloride, mixing the reaction solution with water, separating the aqueous phase of the resultant two-phase mixture, and (b) reacting the organic phase containing (p-tolylsulfonyl)methyl isocyanide direct with a compound of formula II

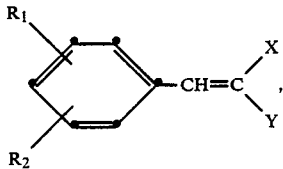

(II)

wherein X, $R_1$ and $R_2$ are as defined for formula I, Y is —CO—NHR$_4$, —CO—R$_5$ or —S—R$_5$, R$_5$ is $C_1$-$C_6$alkyl, $C_1$-$C_6$haloalkyl, phenyl or benzyl, or phenyl or benzyl which are each substituted by halogen, methyl, methoxy or methylthio, and R$_4$ is as defined for formula I, in the presence of a base.

Examples of suitable inert solvents are compounds or mixtures of compounds selected from the group of the open-chain or cyclic ethers for example dioxane, tetrahydrofuran, diethyl ether, diisopropyl ether, dimethoxymethane, 1,2-dimethoxyethane, or from the group of the chloroalkanes, for example methylene chloride, chloroform, or carbon tetrachloride, or compounds selected from the group of the ketones, for example, acetone, methylethylketone, diethylketone, cyclohexanone, methylisopropylketone or methylisobutylketone or from the group of the alkyl esters of lower carbonic acids, for example acetic acid methyl ester, acetic acid ethyl ester or propionic acid ethyl ester. Preferred solvents are tetrahydrofuran, dioxane, dimethoxymethane, acetic acid ethyl ester and 1,2-dimethoxyethane. Particularly preferred solvents are 1,2-dimethoxyethane and acetic acid ethyl ester.

Organic bases suitable for the preparation of (p-tolylsulfonyl)methyl isocyanide from N-(p-tolylsulfonyl)methyl formamide are, for example, quinoline, pyridine or diisopropylamine, preferably tertiary amines such as quinuclidine, N,N-dimethylaniline, dimethylaminopyridine, N-methylpyrrolidine or N,N,N',N'-tetramethylethylenediamine, and, most particularly, trialkylamines such as triethylamine or tri-n-propylamine. Triethylamine is especially preferred.

Examples of suitable bases for the reaction of (p-tolylsulfonyl)methyl isocyanide with the compound of formula II are oxides, hydrides, hydroxides, carbonates, carboxylic acid salts or alcoholates of an alkali metal or alkaline earth metal, trialkylamines or pyridine bases. Particularly suitable bases are sodium methylate, sodium ethylate, aqueous sodium hydroxide, aqueous potassium hydroxide, sodium hydroxide in methanol, potassium hydroxide in methanol, sodium carbonate or potassium carbonate. Particularly preferred bases are aqueous sodium hydroxide, sodium hydroxide in methanol, aqueous potassium hydroxide, potassium hydroxide in methanol and sodium methylate.

In a preferred embodiment of the process of this invention, the compound of formula II is added to the solution of (p-tolylsulfonyl)methyl isocyanide and the base is subsequently added to the reaction mixture.

For the reaction of the compound of formula II with (p-tolylsulfonyl)methyl isocyanide, the base is normally added in an amount of 2 to 3 mol, preferably of 2 to 2.4 mol, per mol of compound of formula II. The reaction of the compound of formula II with (p-tolylsulfonyl)methyl isocyanide normally takes place in the temperature range from −25° to +25° C., the preferred temperature range being from −10° to +10° C.

The compound of formula II and the (p-tolylsulfonyl)methyl isocyanide are conveniently used in equimolar amounts or an excess of 10 to 20 mol % of compound of formula II is used. It is especially preferred to use equimolar amounts.

If ketones or alkyl esters of lower carbonic acids are used as inert solvents in process step (a), it is advantageous to add an aqueous solution of a base to the organic phase and subsequently separate the aqueous phase from the mixture before the performance of process step (b).

Suitables bases for this process variants are, for example, sodium hydroxide, potassium hydroxide, sodium carbonate, sodium hydrogen carbonate and potassium carbonate but in particular sodium hydroxide and sodium carbonate. Acetic acid ethyl ester is especially suitable as an inert solvent for this process variant.

A particularly preferred embodiment of the process of this invention comprises reacting N-(p-tolylsulfonyl)methyl formamide in 1,2-dimethoxyethane with phosphoroxy chloride in the presence of triethylamine, mixing the reaction mixture with the 0.5- to 0.7-fold volume of water, separating the aqueous phase from the resultant two-phase reaction mixture, and reacting the organic phase containing (p-tolylsulfonyl)methyl isocyanide direct with a compound of formula II in the presence of a base.

A further preferred embodiment of the process of the invention comprises using dioxane as inert solvent and mixing the reaction mixture obtained from the reaction of N-(p-tolylsulfonyl)methyl formamide with phosphoroxy chloride with the 0.2-fold to 0.35-fold volume of water.

Another variant of the process of the invention comprises using tetrahydrofuran as solvent and mixing the reaction mixture obtained from the reaction of N-(p-tolylsulfonyl)methyl formamide with phosphoroxy chloride with the 0.3-fold to 0.8-fold volume of water.

A further variant of the process of the invention comprises using dimethoxymethane as inert solvent and mixing the reaction mixture obtained from the reaction of N-(p-tolylsulfonyl)methyl formamide with phosphoroxy chloride with the 0.3-fold to 1.2-fold volume of water.

For the above described embodiments of the process of the invention it is preferred to use compounds of formula II, wherein
Y is —CO—NHR$_4$ or —CO—R$_5$,
R$_4$ is hydrogen or methyl,
R$_5$ is methyl or phenyl,
R$_1$ and R$_2$ are each independently of the other hydrogen or chloro or, when taken together, are methylenedioxy or difluoromethylenedioxy,
X is cyano, —CO—R$_3$ or —CO—OR$_3$, and
R$_3$ is methyl.

The process of this invention makes it possible to prepare compounds of formula I in good yield and in simple manner.

A particular advantage of the process of this invention is that the (p-tolylsulfonyl)methyl isocyanide obtained as intermediate does not need to be isolated from the reaction medium and purified for the reaction with the compound of formula II. The safety risks incurred in isolating and purifying (p-tolylsulfonyl)methyl isocyanide, arising out of a possible explosion of the dried, crystalline product, are totally avoided in the process of this invention. In addition to dispensing with the expensive mode of carrying out the reaction under anhydrous conditions, it must also be singled out for special mention that the substantially simplified handling of (p-tolylsulfonyl)methyl isocyanide afforded by the process of the invention requires fewer safety measures than in the prior art processes.

A further advantage of the process of this invention is that the reaction mixture, upon addition of water, separates into two phases—an organic phase that contains the desired intermediate and an aqueous phase that contains the by-products. Hence the intermediate, after separation of the two phases, is obtained direct in the form of a solution in the solvent employed.

The following Examples illustrate the process of the invention in more detail.

PREPARATORY EXAMPLES

Example P1: 4-Cyano-3-(2,3-dichlorophenyl)pyrrole (a) Preparation of a solution of (p-tolylsulfonyl)methyl isocyanide 41.5 g (0.27 mol) of phosphoroxy chloride are added dropwise over 2 to 3 hours at a temperature of 0° C. to a solution consisting of 55.5 g (0.26 mol) of N-(p-tolylsulfonyl)methyl formamide, 124 g of triethylamine and 155 g of 1,2-dimethoxyethane. The reaction mixture is stirred for 1 hour at 0° C. and then mixed with 220 ml of water while cooling. The temperature of the reaction mixture is allowed to rise to +20° C. and thereafter the lower aqueous phase of the resultant two-phase mixture is separated, to give 157 g of a solution of (p-tolylsulfonyl)methyl isocyanide in 1,2-dimethoxyethane which contains 23.2% by weight of product (72% of theory).

(b) With stirring, 48.3 g of α-cyano-2,3-dichlorocinnamide are added to 157 g of the solution of (p-tolylsulfonyl)methyl isocyanide prepared according to (a). The reaction mixture is cooled to 0° C. and then 53.3 g (0.4 mol) of 30% aqueous sodium hydroxide are added dropwise over 2 hours, with stirring. Stirring is continued for 2 hours at 0° C. and then 200 g of water are added. The reaction solution is then concentrated at +70° C./200 mbar and the product is isolated by filtration after addition of 300 g of water at room temperature. The filter residue is washed with 80 g of toluene and dried under vacuum, affording 44.9 g of 4-cyano-3-(2,3-dichlorophenyl)pyrrole (97% of theory) which melts at 149° C.

Example P2:
4-Cyano-3-(2,3-methylenedioxyphenyl)pyrrole

With stirring, 24.9 g of α-cyano-2,3-methylenedioxycinnamide are added to 96.9 g of a 23.2 % by weight solution of (p-tolylsulfonyl)methyl isocyanide prepared according to Example P1 (a). Then 41.4 g of a 30% solution of sodium methylate in methanol are added dropwise over 2 hours. The mixture is stirred for 30 minutes and then 300 ml of water are added dropwise and the product is isolated by filtration. The filter residue is washed with toluene and dried under vacuum, affording 21 g (86.5% of theory) of 4-cyano-3-(2,3-methylenedioxyphenyl)pyrrole which melts at 206°–208° C.

Example P3:
4-Methylcarbonyl-3-(2.3-dichlorophenyl)pyrrole

With stirring, 20 g of 1,1-di(methylcarbonyl)-2-(2,3-dichlorophenyl)ethene are added at 0° C. to 65 g of a 23.2% by weight solution of (p-tolylsulfonyl)methyl isocyanide prepared according to Example P1 (a). Then 28.1 g of a 30 % solution of sodium methylate in methanol are added dropwise over 3 hours. The mixture is stirred for 60 minutes at a temperature of +10° C. and then 170 ml of water are added dropwise and the product is subsequently isolated by filtration. The filter residue is recrystallised from a 1:1 mixture of methanol/ethanol and dried under vacuum, affording 8.3 g (50% of theory) of 4-methylcarbonyl-3-(2,3-dichlorophenyl)pyrrole which melts at 192°–194° C.

Example P4: 4-Cyano-3-(4-chlorophenyl)pyrrole

With stirring, 28.8 g of α-cyano-4-chlorocinnamide are added at a temperature of 0° C. to 117.4 g of a 23.2% by weight solution of (p-tolylsulfonyl)methyl isocyanide prepared according to Example P1 (a). Then 50.4 g of a 30% solution of sodium methylate in methanol are added dropwise at a temperature of +5° C. over 3 hours. The mixture is stirred for 2 hours and then 70 ml of water are added. Then 50 ml of the solvent mixture are subsequently removed by concentrating the reaction mixture at 50° C. under vacuum. After addition of a further 140 ml of water the reaction mixture is filtered and the filter residue is washed with 30 ml of toluene. Recrystallisation of the dried filter residue from toluene gives 25.4 g (89.5% of theory) of 4-cyano-3-(4-chlorophenyl)pyrrole which melts at 147°–148° C.

Example P5:
4-Methoxycarbonyl-3-(2,3-dichlorophenyl)pyrrole

With stirring, 20 g of methyl α-methylcarbonyl-2,3-dichlorocinnamate are added at 0° C. to a 22 % by weight solution of (p-tolylsulfonyl)methyl isocyanide prepared according to Example P1 (a). Then 26.3 g of a 30% solution of sodium methylate in methanol are added dropwise over 2 hours. The mixture is stirred for 2 hours and then 35 ml of water are added dropwise. The reaction mixture is concentrated at +50° C. under vacuum. After addition of 70 ml of water, the reaction mixture is concentrated once more under vacuum and then filtered. The filter residue is washed with toluene and recrystallised from ethanol, affording 10.8 g (58% of theory) of 4-methoxycarbonyl-3-(2,3-dichlorophenyl)-pyrrole which melts at 200°–201° C.

Example P6: 4-Cyano-3-(2,3-dichlorophenyl)pyrrole (a) 44.5 g of phosphoroxy trichloride are added dropwise over 2 hours at a temperature of −5° C. to a solution consisting of 59.6 g (0.28 mol) of N-(p-tolylsulfonyl)methyl formamide, 134 g of triethylamine and 168 g of tetrahydrofuran. After stirring for 1 hour at 0° C., the reaction mixture is mixed dropwise with 300 ml of water. During this dropwise addition, the temperature is allowed to rise to +20° C. The lower, aqueous phase of the resultant two-phase mixture is separated, to give 198 g of a solution of (p-tolylsulfonyl)methyl isocyanide in tetrahydrofuran which contains 33 g of product.

(b) With stirring, 46.9 g of α-cyano-2,3-dichlorocinnamide are added to 198 g of the solution of (p-tolylsulfonyl)methyl isocyanide prepared according to (a). The reaction mixture is cooled to +5° C. and then, with stirring, 43.6 g of a 50% solution of potassium hydroxide are added dropwise over 90 minutes. The mixture is stirred for 2 hours and then 80 ml of water are added. Then 50 ml of the solvent mixture are removed by evaporation. After addition of a further 150 ml of water, the reaction mixture is concentrated once more and then filtered. The filter residue is washed with toluene and recrystallised from methanol, affording 34.2 g (85% of theory) of 4-cyano-3-(2,3-dichlorophenyl)pyrrole which melts at 146°–148° C.

Example P7: 4-Cyano-3-(2,3-dichlorophenyl)pyrrole (a) Preparation of a solution of (p-tolylsulfonyl)methyl isocyanide 31.5 g of phosphoroxy chloride are added dropwise over 2 hours at a temperature of 0°–5° C. to a solution consisting of 43 g (0.2 mol) of N-(p-tolylsulfonyl)methyl formamide, 92.1 g of triethylamine and 145 g of acetic acid ethyl ester. The reaction mixture is stirred for 30 minutes at 0°–5° C. and then mixed with 150 ml of water. Stirring is continued for 10 minutes at +20° C. and thereafter the aqueous phase is separated. 100 ml of aqueous 1N sodium hydroxide are added and stirring is continued for 10 minutes. The aqueous phase is separated and thereafter the organic phase is washed with 50 ml of water to give 150 g of a solution of (p-tolylsulfonyl)methyl isocyanide in acetic acid ethyl ester which contains 31 g of product.

(b) With stirring, 38.6 g of α-cyano-2,3-dichlorocinnamide are added to 150 g of the solution of (p-tolylsulfonyl)methyl isocyanide prepared according to (a). The reaction mixture is cooled to 0° C. and then 63.2 g of 30% sodium methylate are added dropwise in methanol over 3 hours, with stirring. After 100 ml of water are added, stirring is continued for 15 minutes and thereafter the aqueous phase is separated. After addition of water the solvent is removed completely at reduced pressure at a temperature of from 50°–60° C. The remaining suspension is cooled to room temperature and the product is isolated by filtration. The filter residue is washed with 200 ml of toluene and dried, affording 31 g of 4-cyano-3-(2,3-dichlorophenyl)pyrrole (82% of theory) which melts at 148° C.

Example P8:
4-Cyano-3-(2,3-difluoromethylenedioxy)pyrrole (a) Preparation of a solution of (p-tolylsulfonyl)methyl isocyanide 31.8 g (0.208 mol) of phosphoroxy chloride are added dropwise over 1 to 2 hours at a temperature of 0°–5° C. to a solution consisting of 42.6 g (0.2 mol) of N-(p-tolylsulfonyl)methyl formamide, 96 g of triethylamine and 160 g of acetic acid ethyl ester. The reaction mixture is stirred for 1 hour at 0°–5° C. and then mixed with 150 ml of water. The temperature of the reaction mixture is allowed to rise to +20° C. and thereafter the lower aqueous phase is separated. 100 ml of 10% aqueous sodium carbonate are added and stirring is continued for 10 minutes. Thereafter the aqueous phase is separated to give 210 g of a solution of (p-tolylsulfonyl)methyl isocyanide in acetic acid ethyl ester which contains 33.2 g (85% of theory) of product.

(b) With stirring, 42.8 g (0.17 mol) of α-cyano-2,3-difluoromethylenedioxycinnamide are added to 210 g of the solution of (p-tolylsulfonyl)methyl isocyanide prepared according to (a). The reaction mixture is cooled to 0°–5° C. and then 45.8 g (0.204 mol) of 35% potassium hydroxide in methanol are added dropwise over 1 hour, with stirring. Stirring is continued for 1 hour at +20° C. The preparation can be continued by one of the following methods:

Method 1: 120 ml of the acetic acid ethyl ester/methanol mixture are removed by distillation at a temperature of from 65°–70° C. After addition of 300 ml of methanol the reaction mixture is concentrated once more by evaporation of 170 ml of solvent. After addition of 90 ml of water, the reaction mixture is filtered. The filter residue is washed with a methanol/water mixture affording 35.8 g (85% of theory) of 4-cyano-3-(2,3-difluoromethylenedioxyphenyl)pyrrole which melts at 190°–195° C.

Method 2: 120 ml of the acetic acid ethyl ester/methanol mixture are removed by distillation at a temperature of from 65°–70° C. After addition of 120 ml water the reaction mixture is concentrated once more by evaporation. Thereafter 120 ml of methanol are added and the reaction mixture is filtered. The filter residue is washed with a methanol/water mixture affording 34.3 g (83% of theory) 4-cyano-3-(2,3-difluoromethylenedioxy)pyrrole which melts at 190°–195° C.

Method 3: After addition of 200 ml of water and separating of the aqueous phase 120 ml of acetic acid ethyl ester are removed by destillation. After addition of 300 ml of methanol to the reside the reaction mixture is concentrated once more by evaporation of 170 ml of solvent. After addition of 90 ml of water, the reaction mixture is filtered. The filter residue is washed with a methanol/water mixture affording 34.3 g (83% of theory) of 4-cyano-3-(2,3-difluoromethylenedioxyphenyl)-pyrrole which melts at 190°–195° C.

What is claimed is:

1. A process for the preparation of a 3-phenylpyrrole derivative of formula I

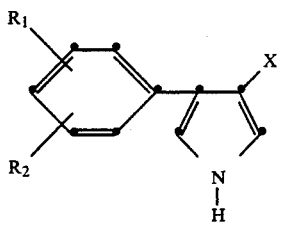

wherein
X is cyano, —CO—R$_3$, —CO—OR$_3$ or

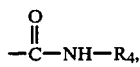

R$_1$ and R$_2$ are each independently of the other hydrogen, C$_1$-C$_6$alkyl,
C$_1$-C$_6$alkoxy, C$_1$14 C$_6$alkylthio, nitro, cyano, halogen or C$_1$-C$_6$haloalkyl, or
R$_1$ and R$_2$, when taken together, are methylenedioxy or difluoromethylenedioxy,
R$_3$ is C$_1$-C$_6$alkyl, C$_1$-C$_6$haloalkyl, phenyl or benzyl, or phenyl or benzyl which are each substituted by halogen, methyl, methoxy or methylthio,
R$_4$ is hydrogen, C$_1$-C$_6$haloalkyl, phenyl or benzyl, or phenyl or benzyl which are each substituted by halogen, methyl, methoxy or methylthio, which process comprises
(a) reacting N-(p-tolylsulfonyl)methyl formamide, in an inert solvent and in the presence of an organic base, with phosphoroxy chloride, mixing the reaction solution with water, separating the aqueous phase of the resultant two-phase mixture, and
(b) reacting the organic phase containing (p-tolylsulfonyl)methyl isocyanide direct with a compound of formula II

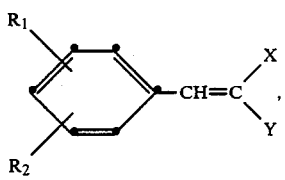

wherein X, R$_1$ and R$_2$ are as defined for formula I, Y is —CO—NHR$_4$, —CO—R$_5$ or —S—R$_5$, R$_5$ is C$_1$-C$_6$alkyl, C$_1$-C$_6$haloalkyl, phenyl or benzyl, or phenyl or benzyl which are each substituted by halogen, methyl, methoxy or methylthio, and R$_4$ is as defined for formula I, in the presence of a base.

2. A process according to claim 1, which comprises
(a) adding the compound of formula II to the solution of (p-tolylsulfonyl)methyl isocyanide, and
(b) adding the base to the reaction mixture.

3. A process according to claim 1, which comprises adding the base in an amount of 2 to 3 mol per mol of compound of formula II in the reaction of (p-tolylsulfonyl)methyl isocyanide with the compound of formula II.

4. A process according to claim 1, wherein R$_1$ and R$_2$ are each independently of the other hydrogen, halogen, methoxy or methylthio or, when taken together, are methylenedioxy or difluoromethylenedioxy, R$_3$ and R$_5$ are independently of each other C$_1$-C$_4$alkyl or C$_1$-C$_4$haloalkyl, R$_4$ is hydrogen, C$_1$-C$_4$alkyl or C$_1$-C$_4$haloalkyl, and Y is —CO—NHR$_4$ or —CO—R$_5$.

5. A process according to claim 1, wherein the compound of formula II is used in an excess of 10 to 20 mol %, based on the amount of (p-tolylsulfonyl)methyl isocyanide.

6. A process according to claim 1, wherein (p-tolylsulfonyl)methyl isocyanide and the compound of formula II are used in equimolar amounts.

7. A process according to claim 1, wherein the inert solvent is a compound or a mixture of compounds selected from the group of the open chain or cyclic ethers, chloroalkanes, ketones or from the group of the alkyl esters of lower carbonic acids.

8. A process according to claim 1, wherein the inert solvent is a compound or a mixture of compounds selected from the group of the open-chain or cyclic ethers or from the group of the chloroalkanes.

9. A process according to claim 1, wherein a tertiary amine is used as base in the reaction of N-(p-tolylsulfonyl)methyl formamide with phosphoroxy chloride.

10. A process according to claim 1, wherein an oxide, hydride, hydroxide, carbonate, carboxylic acid salt or alcoholate of an alkali metal or alkaline earth metal, a trialkylamine or a pyridine base is used as base for the reaction of the solution of (p-tolylsulfonyl)methyl isocyanide with the compound of formula II.

11. A process according to claim 1, wherein the reaction of the compound of formula II with (p-tolylsulfonyl)methyl isocyanide is carried out in the temperature range from −25° to +25° C.

12. A process according to claim 1, wherein the reaction of the compound of formula II with (p-tolylsulfonyl)methyl isocyanide is carried out in the temperature range from −10° to +10° C.

13. A process according to claim 10, wherein the base is sodium methylate, sodium ethylate, aqueous sodium hydroxide, aqueous potassium hydroxide, sodium carbonate or potassium carbonate.

14. A process according to claim 10, wherein the base is used in an amount of 2 to 2.4 mol per mol of compound of formula II.

15. A process according to claim 9, wherein the base is triethylamine.

16. A process according to claim 1, wherein the inert solvent is dimethoxymethane, 1,2-dimethoxyethane, diethyl ether, diisopropyl ether, tetrahydrofuran, dioxane, methylene chloride, chloroform, carbon tetrachloride or acetic acid ethyl ester.

17. A process according to claim 1, wherein the inert solvent is dimethoxymethane, 1,2-dimethoxyethane, diethyl ether, diisopropyl ether, tetrahydrofuran, dioxane, methylene chloride, chloroform or carbon tetrachloride.

18. A process according to claim 1, wherein the inert solvent is dimethoxymethane, 1,2-dimethoxyethane, tetrahydrofuran, dioxane or acetic acid ethyl ester.

19. A process according to claim 1, wherein the inert solvent is dimethoxymethane, 1,2-dimethoxyethane, tetrahydrofuran or dioxane.

20. A process according to claim 1, wherein the inert solvent is 1,2-dimethoxyethane and the reaction mixture obtained after the reaction of N-(p-tolylsulfonyl)methyl formamide with phosphoroxy chloride is mixed with the 0.5- to 0.7-fold volume of water.

21. A process according to claim 1, wherein the inert solvent is dioxane and the reaction mixture obtained from the reaction of N-(p-tolylsulfonyl)methyl formamide with phosphoroxy chloride is mixed with the 0.2- to 0.35-fold volume of water.

22. A process according to claim 1, wherein the inert solvent is tetrahydrofuran and the reaction mixture obtained from the reaction of N-(p-tolylsulfonyl)methyl formamide with phosphoroxy chloride is mixed with the 0.3- to 0.8-fold volume of water.

23. A process according to claim 1, wherein the inert solvent is dimethoxymethane and the reaction mixture obtained from the reaction of N-(p-tolylsulfonyl)methyl formamide with phosphoroxy chloride is mixed with the 0.3- to 1.2-fold volume of water.

24. A process according to claim 1, wherein X is cyano, —CO—OR$_3$ or —CO—R$_3$, R$_1$ and R$_2$ are each independently of the other hydrogen, chlorine or, when taken together, are methylenedioxy or difluoromethylenedioxy, R$_3$ is methyl, Y is —CO—NHR$_4$ or —CO—R$_5$, R$_4$ is hydrogen or methyl, and R$_5$ is methyl or phenyl.

25. A process according to claim 1, which comprises
(a) carrying out the reaction of N-(p-tolylsulfonyl)methyl formamide with phosphoroxy chloride in 1,2-dimethoxyethane in the presence of triethylamine, mixing the reaction mixture with the 0.55- to 0.6-fold volume of water, separating the aqueous phase from the resultant two-phase reaction mixture, and
(b) reacting the organic phase containing (p-tolylsulfonyl)methyl isocyanide with the equimolar amount of compound of formula II, based on the amount of (p-tolylsulfonyl)methyl isocyanide, in the presence of 2 to 2.4 mol of aqueous sodium hydroxide, based on the compound of formula II, in the temperature range from −10° to +10° C.

26. A process according to claim 22, which comprises
(a) adding the compound of formula II to the solution of (p-tolylsulfonyl)methyl isocyanide, and
(b) adding aqueous sodium hydroxide to the reaction mixture.

* * * * *